US00PP23098P2

(12) United States Plant Patent
Lubbe

(10) Patent No.: US PP23,098 P2
(45) Date of Patent: Oct. 2, 2012

(54) ***PENSTEMON* PLANT NAMED 'MARBLE RIDING HOOD'**

(50) Latin Name: *Penstemon schmidel*
Varietal Denomination: Marble Riding Hood

(75) Inventor: Remy Lubbe, Noordwijkerhout (NL)

(73) Assignee: Molter B.V., Noordwijkerhout (NL)

( * ) Notice: Subject to any disclaimer, the term of this patent is extended or adjusted under 35 U.S.C. 154(b) by 9 days.

(21) Appl. No.: 12/931,671

(22) Filed: Feb. 7, 2011

(51) Int. Cl.
*A01H 5/00* (2006.01)

(52) U.S. Cl. ..... Plt./465

(58) Field of Classification Search ..... Plt./465
See application file for complete search history.

*Primary Examiner* — Susan McCormick Ewoldt
(74) *Attorney, Agent, or Firm* — C. A. Whealy

(57) ABSTRACT

A new and distinct cultivar of *Penstemon* plant named 'Marble Riding Hood', characterized by its upright and compact plant habit; vigorous growth habit; freely flowering habit; light red purple and white-colored flowers arranged on strong flowering stems; and good garden performance.

1 Drawing Sheet

Botanical designation: *Penstemon schmidel.*
Cultivar denomination: 'MARBLE RIDING HOOD'.

BACKGROUND OF THE INVENTION

The present invention relates to a new and distinct cultivar of *Penstemon* plant, botanically known as *Penstemon schmidel* and hereinafter referred to by the name 'Marble Riding Hood'.

The new *Penstemon* plant is a product of a planned breeding program conducted by the Inventor in Noordwijkerhout, The Netherlands. The objective of the breeding program is to create new winter-hardy *Penstemon* plants with numerous attractive flowers and long flowering period.

The new *Penstemon* plant originated from a cross-pollination during the spring of 2008 of two unnamed selections of *Penstemon schmidel*, not patented. The new *Penstemon* plant was discovered and selected by the Inventor as a single flowering plant from within the progeny of the stated cross-pollination grown in a controlled environment in Noordwijkerhout, The Netherlands in August, 2009.

Asexual reproduction of the new *Penstemon* plant by vegetative cuttings in Noordwijkerhout, The Netherlands, since August, 2009, has shown that the unique features of this new *Penstemon* plant are stable and reproduced true to type in successive generations.

SUMMARY OF THE INVENTION

Plants of the new *Penstemon* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Marble Riding Hood'. These characteristics in combination distinguish 'Marble Riding Hood' as a new and distinct *Penstemon* plant:

1. Upright and compact plant habit.
2. Vigorous growth habit.
3. Freely flowering habit.

4. Light red purple and white-colored flowers arranged on strong flowering stems.
5. Good garden performance.

Plants of the new *Penstemon* differ from plants of the parent selections in the following characteristics:

1. Plants of the new *Penstemon* are more vigorous than plants of the parent selections.
2. Plants of the new *Penstemon* have stronger flowering stems than plants of the parent selections.
3. Plants of the new *Penstemon* flower for a longer period of time than plants of the parent selections.
4. Plants of the new *Penstemon* are more winter-hardy than plants of the parent selections.

Plants of the new *Penstemon* can be compared to plants of *Penstemon* 'Red Knight', not patented. In side-by-side comparisons conducted in Noordwijkerhout, The Netherlands, plants of the new *Penstemon* differed from plants of 'Red Knight' in the following characteristics:

1. Plants of the new *Penstemon* were more compact and stockier than plants of 'Red Knight'.
2. Plants of the new *Penstemon* had stronger flowering stems than plants of 'Red Knight'.
3. Plants of the new *Penstemon* and 'Red Knight' differed in flower color as plants of 'Red Knight' had red-colored flowers.

Plants of the new *Penstemon* can be compared to plants of *Penstemon schmidel* 'Red Riding Hood', disclosed in U.S. Plant Pat. No. 18,950. In side-by-side comparisons conducted in Noordwijkerhout, The Netherlands, plants of the new *Penstemon* differed primarily from plants of 'Red Riding Hood' in flower color as plants of 'Red Riding Hood' had bright red-colored flowers. In addition, plants of the new *Penstemon* had lighter green-colored stems, leaves and peduncles than plants of 'Red Riding Hood'.

Plants of the new *Penstemon* can also be compared to plants of *Penstemon schmidel* 'Lavender Riding Hood', disclosed in a U.S. Plant patent application Ser. No. 12/931,672 filed concurrently. In side-by-side comparisons conducted in Noordwijkerhout, The Netherlands, plants of the new *Penstemon* differed primarily from plants of 'Lavender Riding Hood' in flower color as plants of 'Lavender Riding Hood' had darker-colored flowers than plants of the new *Penstemon*.

BRIEF DESCRIPTION OF THE PHOTOGRAPH

The accompanying colored photograph illustrates the overall appearance of the new *Penstemon* plant showing the colors as true as it is reasonably possible to obtain in colored reproductions of this type. Colors in the photograph may differ slightly from the color values cited in the detailed botanical description which accurately describe the actual colors of the new *Penstemon* plant.

The photograph comprises a side perspective view of a typical flowering plant of 'Marble Riding Hood' grown in a container.

DETAILED BOTANICAL DESCRIPTION

Plants used for the aforementioned photograph and following description were grown during the summer in an outdoor nursery in Noordwijkerhout, The Netherlands and under typical production practices and conditions. During the production of the plants, day temperatures ranged from 20° C. to 33° C. and night temperatures ranged from 12° C. to 20° C. Plants were five months old when the photograph and the description were taken. In the following description, color references are made to The Royal Horticultural Society Colour Chart, 2001 Edition, except where general terms of ordinary dictionary significance are used.

Botanical classification: *Penstemon schmidel* 'Marble Riding Hood'.

Parentage:

*Female parent*.—Unnamed selection of *Penstemon schmidel*, not patented.

*Male parent*.—Unnamed selection of *Penstemon schmidel*, not patented.

Propagation:

*Type cutting*.—By vegetative cuttings.

*Time to initiate roots*.—About eight to ten days at 20° C. to 22° C.

*Root description*.—Fine, fibrous; color, close to 161D.

*Rooting habit*.—Dense.

Plant description:

*Plant form and growth habit*.—Perennial; upright and compact plant form; narrow inverted triangle; vigorous growth habit and relatively rapid growth rate.

*Plant height*.—About 30 cm.

*Plant width*.—About 15 cm to 20 cm.

*Lateral branch description*.—Quantity: Freely branching habit with about 16 lateral branches developing per plant. Length: About 30 cm. Diameter: About 3 mm. Internode length: About 4.8 cm. Strength: Strong. Texture: Smooth, glabrous. Color: Close to 148C.

Foliage description:

*Arrangement*.—Opposite, simple; sessile.

*Length*.—About 6 cm to 7 cm.

*Width*.—About 1.5 cm to 2 cm.

*Shape*.—Lanceolate.

*Apex*.—Acuminate.

*Base*.—Truncate, oblique.

*Margin*.—Entire.

*Texture, upper and lower surfaces*.—Smooth, glabrous.

*Venation pattern*.—Pinnate.

*Color*.—Developing and fully expanded leaves, upper surface: Close to 148B; venation, close to 145C. Developing and fully expanded leaves, lower surface: Close to 147B; venation, close to 145C.

Flower description:

*Flower shape, arrangement and flowering habit*.—Single bi-labiate flowers arranged on terminal racemes; flowers face mostly outwardly; freely flowering with about 70 to 150 flowers developing per inflorescence.

*Fragrance*.—None detected.

*Natural flowering season*.—Long flowering period, plants flower during the summer in The Netherlands.

*Flower longevity on the plant*.—About two weeks; flowers not persistent.

*Flower buds*.—Length: About 6 mm. Diameter: About 4 mm. Shape: Ovoid. Color: Close to 145D.

*Flowers*.—Diameter: About 2.4 cm. Depth (height): About 3.1 cm.

*Petals*.—Arrangement: Five, fused into a tube; bi-labiate, upper lip with two upper petals and lower lip with three lower petals. Length: About 6 mm. Width: About 4 mm. Shape: Ovate to obovate. Apex: Rounded. Margin: Entire. Texture, upper and lower surfaces: Smooth, glabrous; satiny. Color: When opening and fully opened, upper surface: Close to 65B and N155B; towards the base, close to 65A; color becoming closer to 65A with development. When opening and fully opened, lower surface: Close to 65B and N155B; towards the base, close to 65A; color becoming closer to 65A with development.

*Sepals*.—Arrangement: Four sepals in a single whorl; calyx salverform. Length: About 3 mm. Width: About 2 mm. Shape: Round. Apex: Acute. Base: Truncate. Margin: Entire. Texture, upper and lower surfaces: Smooth, glabrous. Color: Immature and mature, upper surface: Close to 144B. Immature and mature, lower surface: Close to 144A.

*Peduncles*.—Length: About 30 cm. Diameter: About 3 mm. Aspect: Upright to about 30° from vertical. Strength: Strong. Texture: Smooth, glabrous. Color: Close to 138C.

*Pedicels*.—Length: About 1.8 cm. Diameter: About 1.5 mm. Aspect: About 10° from the peduncle axis. Strength: Strong. Texture: Smooth, glabrous. Color: Close to 138B.

*Reproductive organs*.—Stamens: Quantity per flower: Four. Anther shape: Oval. Anther length: About 2 mm. Anther color: Close to 202A. Pollen amount: Scarce to moderate. Pollen color: Close to 158B. Pistils: Quantity per flower: One. Pistil length: About 3.3 cm. Stigma shape: Somewhat conical. Stigma color: Close to 155B. Style length: About 2.9 cm. Style color: Close to N155B. Ovary color: Close to 147B.

*Seed/fruit*.—Seed and fruit production have not been observed on plants of the new *Penstemon*.

Disease/pest resistance: Plants of the new *Penstemon* have not been noted to be resistant to pathogens and pests common to *Penstemon*.

Garden performance: Plants of the new *Penstemon* have exhibited good tolerance to rain and wind and have been observed to tolerate temperatures ranging from about −10° C. to about 35° C.

It is claimed:

1. A new and distinct *Penstemon* plant named 'Marble Riding Hood' as illustrated and described.

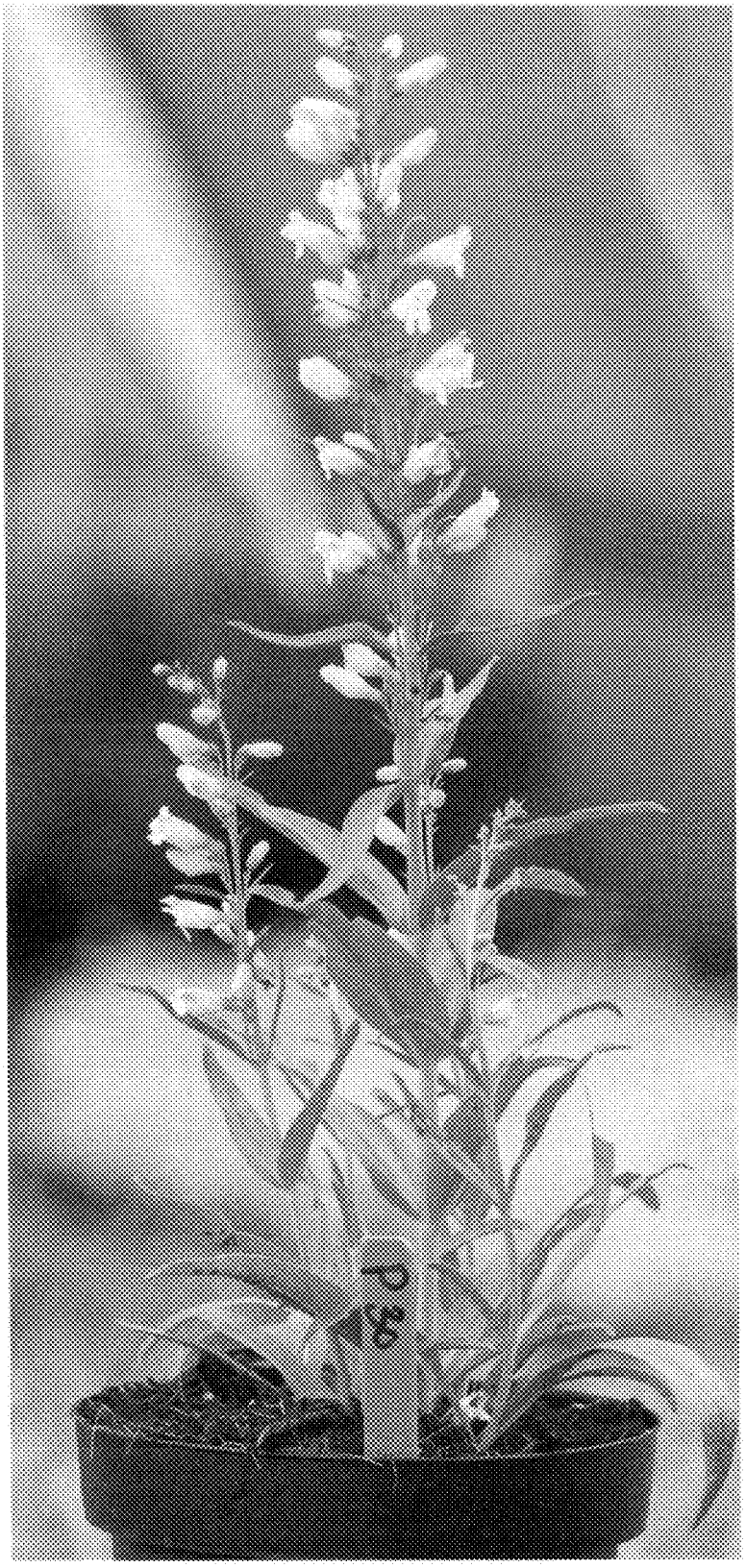

* * * * *